(12) United States Patent
Stefan et al.

(10) Patent No.: US 7,783,099 B1
(45) Date of Patent: Aug. 24, 2010

(54) VIRTUAL COSMETIC AND RECONSTRUCTIVE SURGERY

(75) Inventors: David B. Stefan, Chesapeake, VA (US); David A. Gilbert, Virginia Beach, VA (US)

(73) Assignee: Novaptus Systems, Incorporated, Chesapeake, VA (US)

( * ) Notice: Subject to any disclaimer, the term of this patent is extended or adjusted under 35 U.S.C. 154(b) by 267 days.

(21) Appl. No.: 12/218,511

(22) Filed: Jul. 16, 2008

Related U.S. Application Data (63) Continuation-in-part of application No. 10/979,630, filed on Nov. 1, 2004, now Pat. No. 7,424,139.

(51) Int. Cl.
*G06K 9/00* (2006.01)

(52) U.S. Cl. .................. 382/128; 382/131; 382/100; 382/225; 600/407; 600/427; 600/439; 600/523; 345/619

(58) Field of Classification Search .................. 382/128, 382/131, 225, 262; 345/735, 751, 756, 155; 600/411, 427; 709/107, 204, 223, 219, 315
See application file for complete search history.

(56) References Cited

U.S. PATENT DOCUMENTS

| 5,687,737 | A | * | 11/1997 | Branham et al. ............ 600/523 |
| 5,704,791 | A | * | 1/1998 | Gillio ........................ 434/262 |
| 5,882,206 | A | * | 3/1999 | Gillio ........................ 434/262 |
| 6,161,080 | A | | 12/2000 | Aouni-Ateshian et al. |
| 6,190,320 | B1 | | 2/2001 | Lelong |
| 6,556,236 | B1 | | 4/2003 | Swift et al. |
| 6,608,628 | B1 | | 8/2003 | Ross et al. |
| 7,236,817 | B2 | * | 6/2007 | Papas et al. ................. 600/427 |
| 7,424,139 | B1 | * | 9/2008 | Stefan et al. ................ 382/128 |
| 7,587,075 | B1 | * | 9/2009 | Stefan et al. ................ 382/128 |
| 2002/0009214 | A1 | | 1/2002 | Arima et al. |
| 2002/0035458 | A1 | | 3/2002 | Kim et al. |
| 2002/0064302 | A1 | | 5/2002 | Massengill |

OTHER PUBLICATIONS

Novaptus Offers New Way of Measuring Body Contours; *Hampton Roads Edition M.D. News Special Feature*; Anne A. Abraham; May 2004.

* cited by examiner

*Primary Examiner*—Wes Tucker
*Assistant Examiner*—Nancy Bitar
(74) *Attorney, Agent, or Firm*—Bowman Green Hampton & Kelly, PLLC (57) ABSTRACT

Virtual surgery systems, methods, and apparatuses that provide for the prediction, evaluation, and validation of various cosmetic and reconstructive surgical procedures. The virtual surgery systems, methods, and apparatuses utilize a scanner, measurement software, queries to a postoperative patient scan catalog, conversion of a preoperative image to a Virtual Reality Modeling Language (3-D) image, grafting and scaling of chosen postoperative surgery candidates, conversion from the converted 3-D image to a scanner readable format, and measuring the forecasted 3-D image.

9 Claims, 13 Drawing Sheets

Display All Measurements   Units : cm
Top_Of_Head_Height : 168.54
Bust_Full : 102.72
Bust_Full(Contoured) : 102.88
Bust_Height : 128.65
Bust_Width : 32.
Bust_Prominance_Left : 27.08
Bust_Prominance_Right : 27.55
Underbust_Full : 89.68
Underbust_Width : 31.61
Underbust_Height : 121.65
FrontNeck2Bust_Left : 22.34
FrontNeck2Bust_Right : 22.81
SideNeck2Bust_Left : 26.65
SideNeck2Bust_Right : 27.2
Neck2BustLine_Front : 20.19
Neck2BustLine_Back : 25.67
BustToWaist_Left : 16.89
BustToWaist_Right : 16.31
Bust2Bust_Horizontal : 20.81
Chest_Full : 100.15
Chest_Height : 131.15
Chest_Width : 34.26
Waist_Full : 86.53
Waist_Width : 30.55
Waist_Height_Back : 111.72
Waist_Height_Front : 112.89
Waist_to_Hips_Left : 19.95
Waist_to_Hips_Right : 17.57
Waist_to_Hips_Front : 16.95
Waist_to_Hips_Back : 16.35
Hips_Full : 104.6
Hips_Height : 96.15
Hips_Width : 38.23
Seat_Full : 103.78
Seat_Height : 91.65
Seat_Width : 38.45
Abdomen_Full : 96.42
Abdomen_Height : 106.15
Abdomen_Width : 34.86
Stomach_Full : 91.97
Stomach_Height : 122.15
Stomach_Width : 32.11
Thigh_Left : 60.64
Thigh_Right : 60.61
Outseam_Left : 112.89
Outseam_Right : 112.73
Inseam_Left : 81.64
Inseam_Right : 81.63
Neck_Full : 42.71
Right_Biceps : 30.84
Right_Forearm : 28.83
Right_Wrist : 20.18
Left_Biceps : 30.92
Left_Forearm : 30.32
Left_Wrist : 20.1
Shirt_Sleeve_Left : 86.64
Shirt_Sleeve_Right : 85.37
Bulk_Volume : 12.02
Torso_Slice_File : 158.26

Display All Measurements   Units : cm
Top_Of_Head_Height : 167.04
Bust_Full : 101.73
Bust_Full(Contoured) : 104.62
Bust_Height : 125.65
Bust_Width : 32.72
Bust_Prominance_Left : 29.96
Bust_Prominance_Right : 29.66
Underbust_Full : 80.64
Underbust_Width : 29.34
Underbust_Height : 117.15
FrontNeck2Bust_Left : 24.08
FrontNeck2Bust_Right : 24.65
SideNeck2Bust_Left : 29.71
SideNeck2Bust_Right : 29.54
Neck2BustLine_Front : 21.86
Neck2BustLine_Back : 27.21
BustToWaist_Left : 15.64
BustToWaist_Right : 15.12
Bust2Bust_Horizontal : 22.8
Chest_Full : 96.67
Chest_Height : 138.9
Chest_Width : 37.95
Waist_Full : 85.73
Waist_Width : 30.21
Waist_Height_Back : 110.22
Waist_Height_Front : 111.39
Waist_to_Hips_Left : 20.18
Waist_to_Hips_Right : 17.7
Waist_to_Hips_Front : 16.99
Waist_to_Hips_Back : 16.38
Hips_Full : 104.59
Hips_Height : 94.65
Hips_Width : 38.22
Seat_Full : 103.8
Seat_Height : 90.15
Seat_Width : 38.43
Abdomen_Full : 96.41
Abdomen_Height : 104.65
Abdomen_Width : 34.85
Stomach_Full : 96.38
Stomach_Height : 121.15
Stomach_Width : 32.12
Thigh_Left : 60.64
Thigh_Right : 60.69
Outseam_Left : 111.49
Outseam_Right : 111.29
Inseam_Left : 80.23
Inseam_Right : 80.13
Neck_Full : 42.52
Right_Biceps : 30.84
Right_Forearm : 28.83
Right_Wrist : 20.18
Left_Biceps : 30.91
Left_Forearm : 30.32
Left_Wrist : 20.11
Shirt_Sleeve_Left : 86.83
Shirt_Sleeve_Right : 85.14
Bulk_Volume : 12.43
Torso_Slice_File : 158.97

VIRTUAL COSMETIC AND RECONSTRUCTIVE SURGERY

CROSS-REFERENCE TO RELATED APPLICATIONS

This is a Continuation-In-Part of U.S. patent application Ser. No. 10/979,630, filed Nov. 1, 2004 now U.S. Pat. No. 7,424,139, the disclosure of which is incorporated herein by reference.

BACKGROUND OF THE INVENTION

Field of the Invention

This invention relates generally to cosmetic and reconstructive surgery. In particular, the present invention relates to an improved virtual cosmetic and reconstructive surgery systems, methods, and apparatuses.

SUMMARY OF THE INVENTION

The present invention relates generally to cosmetic and reconstructive surgery. In particular, the present invention relates to an improved virtual cosmetic and reconstructive surgery systems, methods, and apparatuses.

Known methods for evaluating patients and potential patients for cosmetic and reconstructive surgery are not able to provide the patients and potential patients with accurate forecasting and modeling of expected results and outcomes.

The virtual surgery systems, methods, and apparatuses allow a user to predict, evaluate, and validate various cosmetic and reconstructive surgical procedures. In an illustrative, non-limiting embodiment of this invention, the virtual surgery systems, methods, and apparatuses allow a user to predict, evaluate, and validate various breast augmentation surgical procedures.

In an illustrative, non-limiting embodiment of this invention, the virtual surgery systems, methods, and apparatuses utilize a scanner, such as, for example, a white light scanner, measurement software, queries to a postoperative patient scan catalog, conversion of the preoperative image to a Virtual Reality Modeling Language (VRML) image or other similar native three-dimensional (3-D) modeling image, grafting and scaling of chosen postoperative breast candidates, conversion from the converted 3-D image to a format readable by the scanner, and finally, measuring the forecasted 3-D image with certain scanner measurement software.

After a surgical procedure is performed, postoperative scans of the patient are compared to the forecasted 3-D images for validation purposes. The postoperative scan or scans may be added to the catalog of postoperative patients.

Accordingly, this invention provides virtual surgery systems, methods, and apparatuses, which are capable of evaluating patients and potential patients for cosmetic and reconstructive surgery.

This invention separately provides virtual surgery systems, methods, and apparatuses, which provide patients and potential patients for cosmetic and reconstructive surgery with accurate forecasting and modeling of expected results and outcomes.

This invention separately provides virtual surgery systems, methods, and apparatuses, which allow a user to predict, evaluate, and validate various cosmetic and reconstructive surgical procedures.

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein like reference numerals refer to like parts throughout the several views, and wherein.

DETAILED DESCRIPTION OF AN EXEMPLARY EMBODIMENT

For simplicity and clarification, the design factors and operating principles of the virtual surgery systems, methods, and apparatuses according to this invention are explained with reference to various exemplary embodiments of virtual surgery systems, methods, and apparatuses according to this invention. The basic explanation of the design factors and operating principles of the virtual surgery systems, methods, and apparatuses is applicable for the understanding, design, and operation of the virtual surgery systems, methods, and apparatuses of this invention.

Furthermore, it should be appreciated that, for simplicity and clarification, the embodiments of this invention will be described with reference to the prediction, evaluation, and validation of an exemplary breast augmentation surgical procedure. However, it should be appreciated that the virtual surgery systems, methods, and apparatuses of this invention may be utilized in various other cosmetic and reconstructive surgical procedures.

Thus, it should be appreciated that the systems, methods, and apparatuses of this invention may be implemented to predict, evaluate, and validate any type of cosmetic or reconstructive surgical procedures.

It should also be appreciated that the term "virtual surgery" is for basic explanation and understanding of the operation of the virtual surgery systems, methods, and apparatuses of this invention. Therefore, the term "virtual surgery" is not to be construed as limiting the virtual surgery systems, methods, and apparatuses of this invention.

Figure 1A:
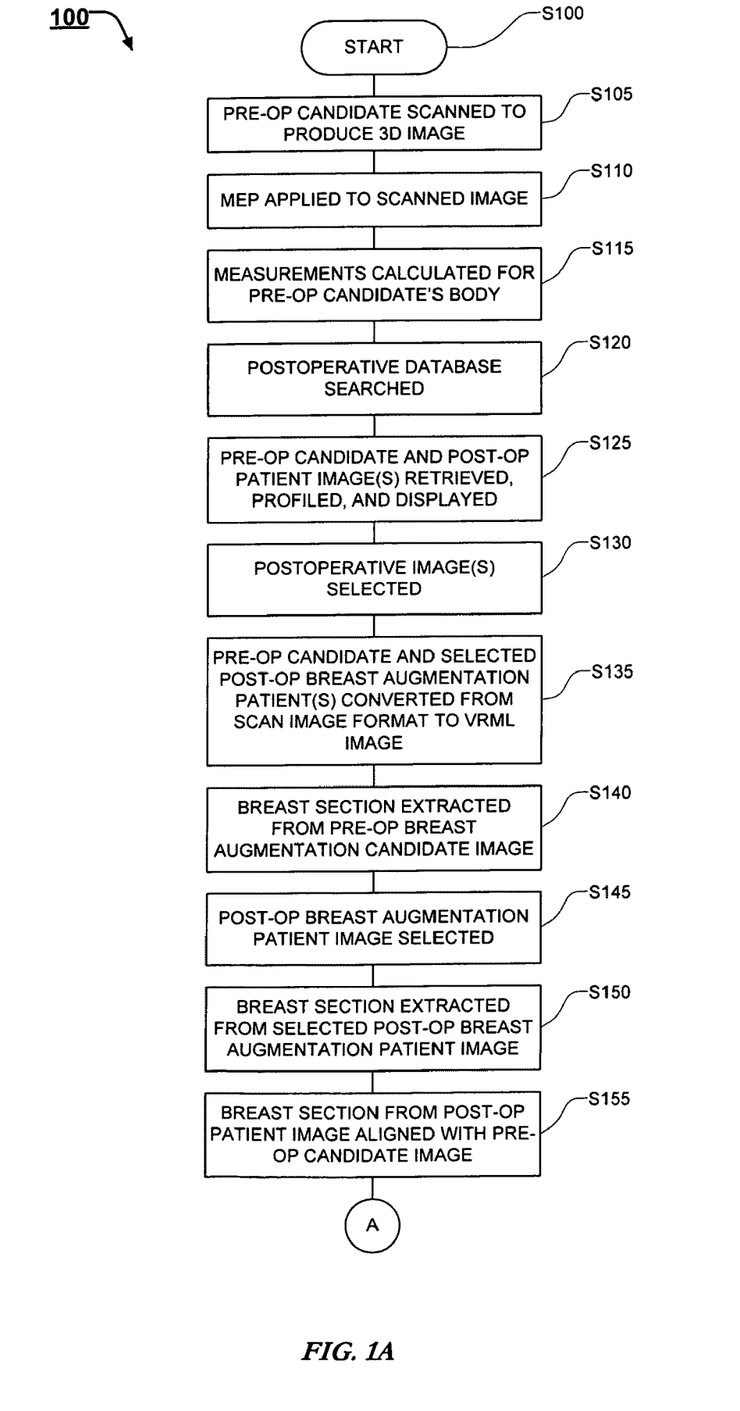
FIGS. 1A and 1B show a flowchart outlining one exemplary embodiment of a method for performing virtual surgery according to this invention.
Figure 1B:
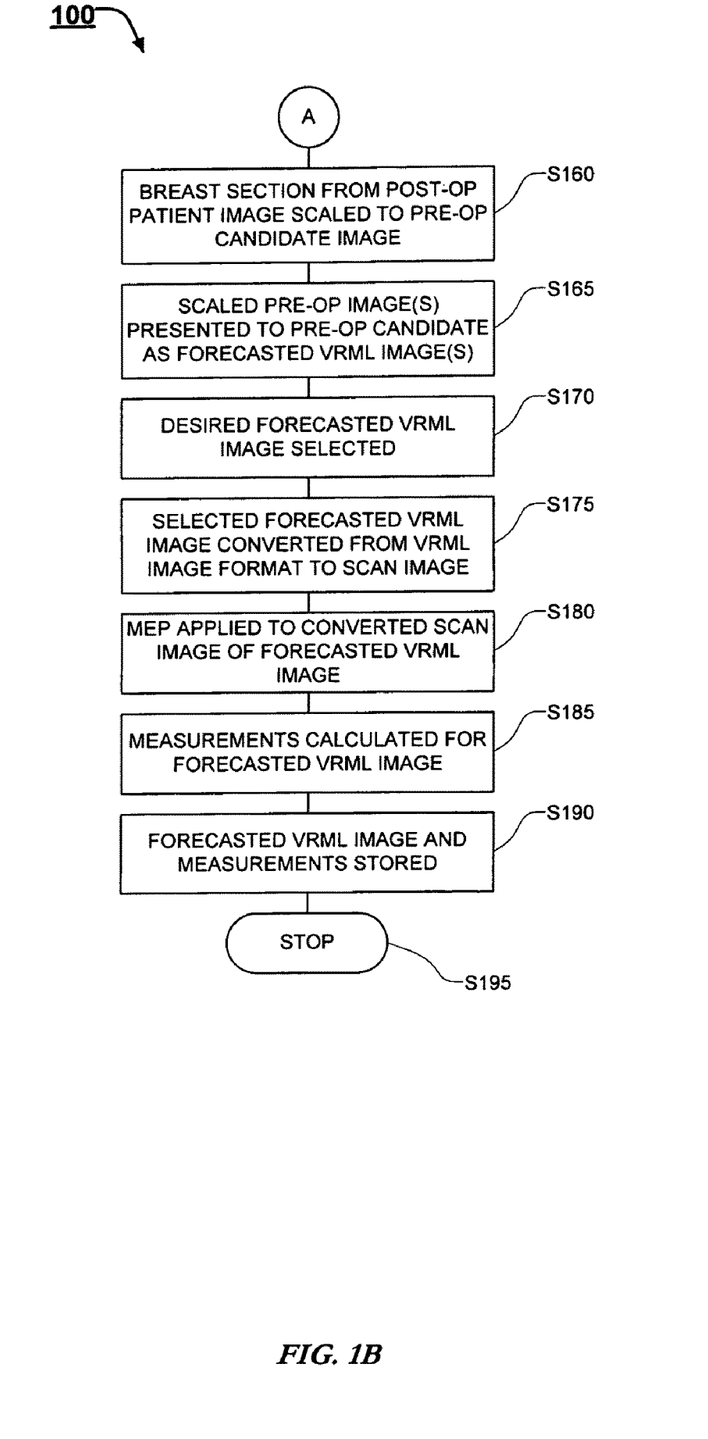

FIGS. 1A and 1B show a flowchart 100 outlining one illustrative, non-limiting embodiment of a method for performing virtual surgery according to this invention.

As shown in FIGS. 1A and 1B, the exemplary method begins in step S100 and continues to Step S105 wherein a preoperative candidate's body is scanned to produce a highly accurate, dimensionally correct, 3-D image of the preoperative candidate's body. In various exemplary embodiments, a white light scanner is used to produce the scanned image. However, it should be appreciated that in various exemplary embodiments, and laser, ultrasonic, or other appropriate scanner, capable of providing a highly accurate, dimensionally correct, 3-D image of the preoperative candidate's body may be used.

Then, in Step S110, a specialized Measurement Extraction Profile (MEP) is applied to the preoperative candidate's scanned image. This MEP file contains instructions for determining specific measurements of the preoperative candidate's scanned image.

Next, in Step S115, the MEP file is used to calculate key measurements of the preoperative candidate's scanned image, such as, for example, of the patient's breasts, waist, hips, abdomen, and stomach. Additionally, certain straight line measurements are calculated for the chest, bust, underbust, waist, hips, abdomen, and stomach. These straight line measurements form the guidelines for selecting appropriate postoperative breast augmentation patients.

In Step S120, a postoperative catalog database is searched for previously scanned and measured postoperative breast augmentation patients whose key measurements, as determined by the MEP file, are similar to the key measurements of the preoperative candidate. In various exemplary embodiments, certain chest, bust, underbust, abdominal, and other straight line and/or width measurements are compared between the preoperative candidate and the cataloged postoperative breast augmentation patients to determine similar key measurements.

In various exemplary embodiments, the database is not searched for exact measurement matches. Rather, the search and comparison parameters are such that postoperative catalog database candidates having selected measurements within a specified range are identified.

In various exemplary embodiments, additional information may be associated with the postoperative patient's scan image. For example, information regarding the implant sizes that the postoperative patient received, the postoperative patient's age at the time of the procedure, any relevant medical data that indicates special conditions that the postoperative patient may have that could eliminate the candidate for consideration, and the like.

In Step S125, the preoperative candidate's scanned image and the appropriate postoperative patients' scanned images are retrieved, profiled, and displayed.

In Step S130, one or more appropriate postoperative breast augmentation patients are selected from the retrieved possible postoperative patients from the postoperative catalog database. The appropriate postoperative breast augmentation patients may be selected based on, for example, prospective candidates whose breast shape and size appeals to the preoperative candidate, makes aesthetic sense, and have similar dimensional widths as the preoperative candidate. Additional information associated with the postoperative patient's scan image may also be used to determine the appropriate postoperative breast augmentation patients.

It should be appreciated that in certain exemplary embodiments, a surgeon or other user may search the postoperative catalog database and select appropriate postoperative patients. In other exemplary embodiments, the preoperative candidate, with or without the assistance of the surgeon, may search the postoperative catalog database and select appropriate postoperative patients. In still other exemplary embodiments, the search and selection may be performed either partially or entirely by an appropriate software program.

In Step S135, the preoperative candidate's scanned image and the one or more selected postoperative breast augmentation patients' scanned images are converted from the scanned image format to a 3-D image format and imported into a 3-D image editor.

Then, in Step S140, using the 3-D image editor, an appropriate breast section is extracted from the torso of the preoperative candidate's 3-D image. It should be appreciated that in certain exemplary embodiments, a surgeon or other user may extract the appropriate breast section from the torso of the preoperative candidate's 3-D image. In other exemplary embodiments, the appropriate breast section may be extracted from the torso of the preoperative candidate's 3-D image either partially or entirely by an appropriate software program.

In various exemplary embodiments, selection of the appropriate breast section to be extracted is based on measurements that define the chest area and the abdominal/waist area of the preoperative candidate's 3-D image.

In Step S145, one of the one or more selected postoperative breast augmentation patients is selected and, in Step S150, an appropriate breast section is extracted from the torso of the selected postoperative breast augmentation patient's 3-D image using the 3-D image editor. It should be appreciated that in certain exemplary embodiments, a surgeon or other user may extract an appropriate breast section from the torso of the selected postoperative patient's 3-D image. In other exemplary embodiments, the appropriate breast section may be extracted from the torso of the selected postoperative breast augmentation patient's 3-D image either partially or entirely by an appropriate software program.

In various exemplary embodiments, selection of the appropriate breast section to be extracted is based on measurements that define the chest area and the abdominal/waist area of each postoperative breast augmentation patient's 3-D image.

Next, in Step S155, the postoperative breast augmentation patient's breast section is aligned within the preoperative candidate's 3-D image. In various exemplary embodiments, a surgeon or other user may align the breast section within the preoperative candidate's 3-D image. In other exemplary embodiments, the appropriate breast section may be aligned within the preoperative candidate's 3-D image either partially or entirely by an appropriate software program.

In Step S160, the postoperative breast augmentation patient's breast section is scaled, if necessary, to match the preoperative candidate's torso. Scaling is typically necessary if the extracted breast section of the postoperative breast augmentation patient is dimensionally different from that of the preoperative candidate's image. In various exemplary embodiments, the postoperative breast augmentation patient's breast section is scaled using a proportional scaling tool to enlarge the breast section in the X, Y, and Z axis to match the dimensions of the torso of the preoperative candidate's 3-D image. When proportional scaling is used, the implant sizes of the postoperative breast augmentation patient's implants are also proportionally scaled.

In various exemplary embodiments, a surgeon or other user may scale the breast section within the preoperative candidate's 3-D image. In other exemplary embodiments, the appropriate breast section may be scaled within the preoperative candidate's 3-D image either partially or entirely by an appropriate software program.

Then, in Step S165, the preoperative candidate's image, with the postoperative breast augmentation patient's breast section having been aligned and scaled within the preoperative candidate's 3-D image, is presented to the preoperative candidate as a forecasted 3-D image of the preoperative candidate after the breast augmentation procedure is complete.

It should be appreciated that the steps of selecting one of the one or more selected postoperative breast augmentation patients; extracting an appropriate breast section from the selected postoperative breast augmentation patient's 3-D image; aligning the postoperative breast augmentation patient's breast section within the preoperative candidate's 3-D image; scaling the postoperative breast augmentation patient's breast section, if necessary, to match the preoperative candidate's torso; and presenting the preoperative candidate's image, with the postoperative breast augmentation patient's breast section having been aligned and scaled within the preoperative candidate's 3-D image, to the preoperative candidate as a forecasted 3-D image (Step S145 through Step S165) may be repeated, as necessary, for any of the remaining one or more selected postoperative breast augmentation patients' 3-D images. In this manner a number of forecasted 3-D images may be developed, which reflect different breast augmentation sizes and/or procedures based on selections from the postoperative breast augmentation catalog.

Thus, in Step S165, the preoperative candidate may be presented with a number of forecasted 3-D images to review.

In Step S170, the preoperative candidate may review the forecasted 3-D images, either alone or together with a surgeon, and select the best overall aesthetic forecasted 3-D image that meets the desires of the patient, and the surgical guidelines, given the preoperative candidate's overall body condition.

In Step S175, once a forecasted 3-D image is selected, the selected forecasted 3-D image is converted from a 3-D image to a format that a scanner can read and measure. In various exemplary embodiments, this is accomplished via a data converter. The data converter takes the forecasted 3-D image, which is in 3-D format, such as, for example a VRML format, and converts the forecasted 3-D image into a format that the scanner can interpret.

In Step S180, once a forecasted 3-D image has been converted into a scanner readable format, the specialized MEP file, as applied in Step S110, is applied to the converted forecasted 3-D image.

In Step S185, the specialized MEP file is used to measure the converted forecasted 3-D image and calculate specific measurements of the preoperative candidate's converted forecasted 3-D image.

Then, in Step S190, once the specific measurements of the preoperative candidate's converted forecasted 3-D image have been calculated, the converted forecasted 3-D image and the measurements become part of the preoperative candidate's digital archive.

The method then advances to Step S195 and the method ends.

It should be appreciated that each preoperative candidate may have a digital archive established to allow information regarding the preoperative candidate or patient, such as, for example, the preoperative candidate/patient's various scans, images, and models, to be archived. Each digital archive may allow the preoperative candidate/patient and/or doctors, surgeons, or other health-care providers easy reference to the preoperative candidate/patient's various scans, images, and models.

In various exemplary embodiments, the entire virtual surgery process, as outlined herein, may be maintained in a digital archive and used as part of a patient maintenance program. As additional scans, images, and/or models of the preoperative candidate/patient created, the digital archive and the patient maintenance program may be utilized, even apart from any surgical aspect, to provide an initial baseline and then allow for monitoring of the preoperative candidate/patient's recovery, growth, and development over time.

It should be appreciated that although the method described above includes archiving, in Step S190, the converted forecasted 3-D image and the measurements as part of the preoperative candidate's digital archive, each scan, image, and/or model created of or for the preoperative candidate/patient may be included as part of the preoperative candidate/patient's digital archive.

Furthermore, if the preoperative candidate does have the surgical procedure, postoperative scans of the preoperative candidate may be compared to the converted forecasted 3-D image and the measurements for validation and so that any discrepancies may be identified and noted in appropriate digital archive data fields.

In various exemplary embodiments, the preoperative candidate's postoperative scan may also be added to the breast augmentation catalog to be used to build future forecasted 3-D images for other preoperative candidates.

Figure 2:
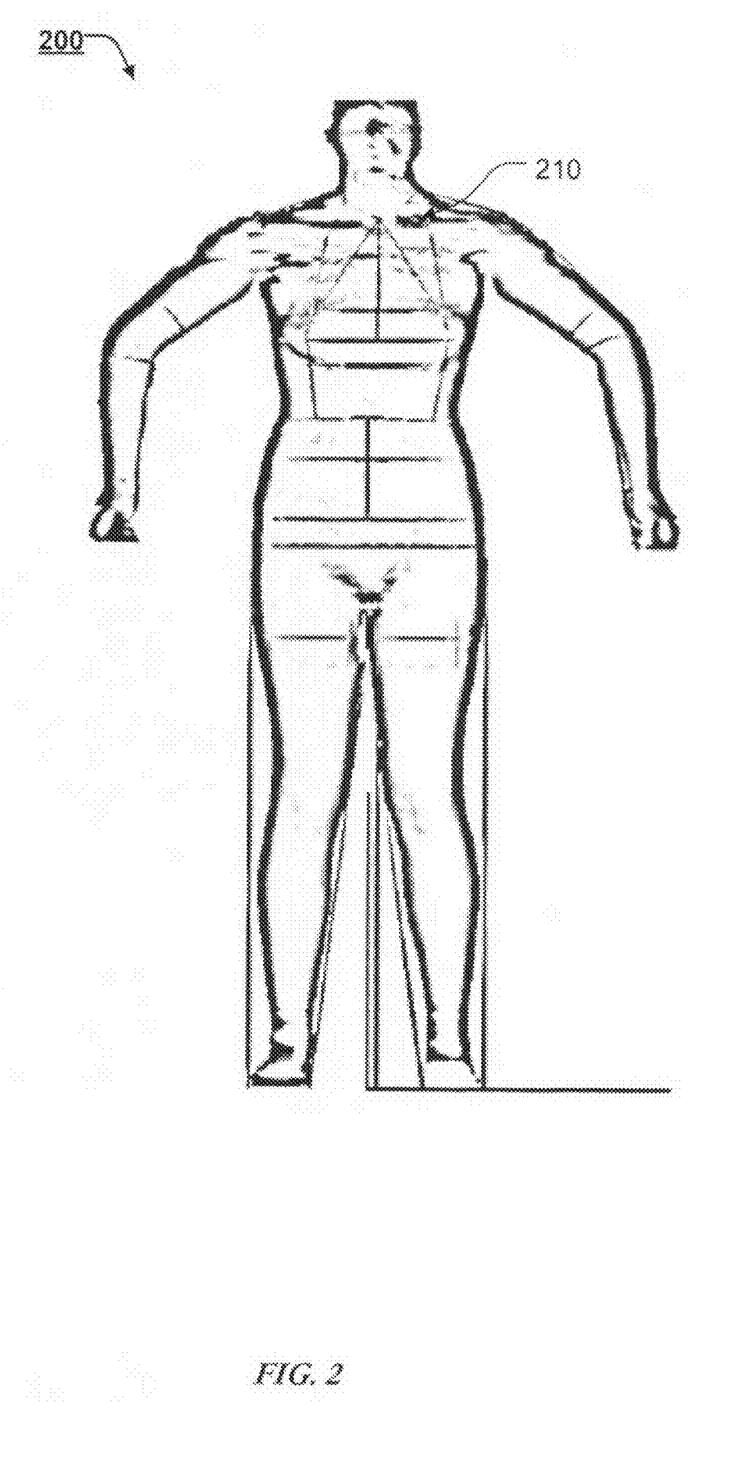
FIG. 2 shows a first exemplary embodiment of a scanned preoperative image of a preoperative candidate with measurement lines according to this invention.
Figure 3:
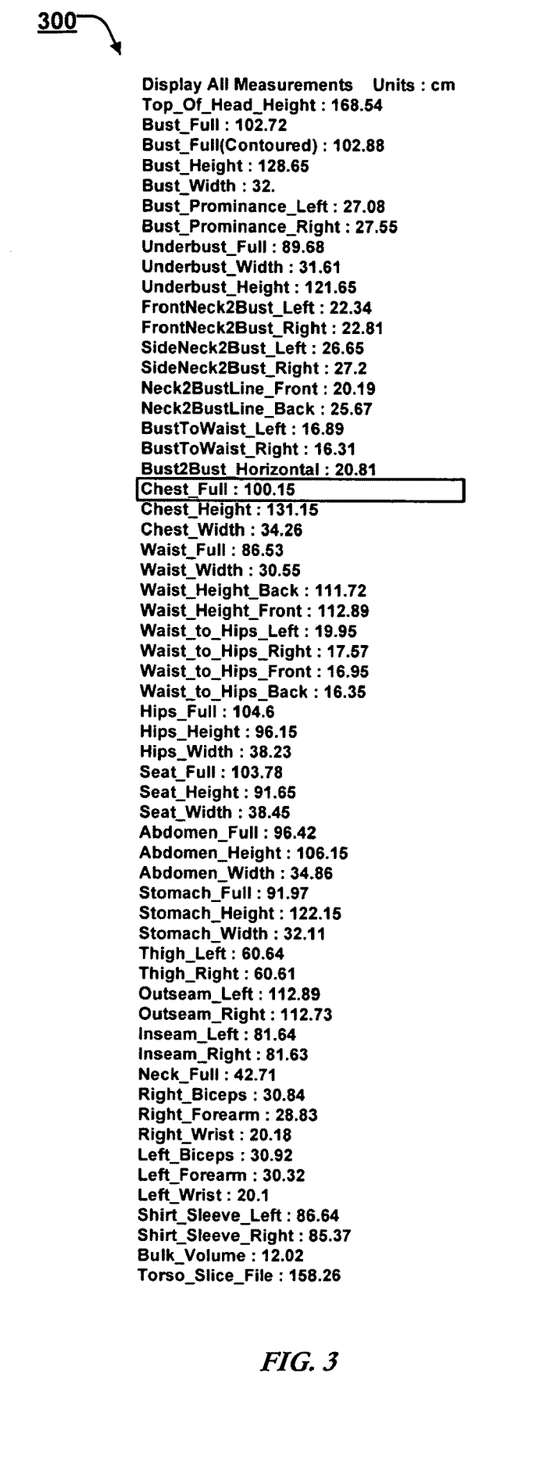
FIG. 3 shows a chart outlining preoperative extracted measurements extrapolated from the scanned preoperative image of FIG. 2 according to this invention.

FIG. 2 shows a first exemplary embodiment of a scanned preoperative image 200 of a preoperative candidate with measurement lines 210 according to this invention, while FIG. 3 shows a chart 300 outlining preoperative extracted measurements extrapolated from the scanned preoperative image 200 of FIG. 2 according to this invention.

As shown in FIG. 2, a preoperative candidate's body has been scanned to produce a highly accurate, dimensionally correct, 3-D image 200 of the preoperative candidate's body. In various exemplary embodiments, a white light scanner is used to produce the scanned image 200. However, it should be appreciated that in various exemplary embodiments, a laser scanner, an ultrasonic imager, or any other known or later developed device useable for producing a highly accurate, dimensionally correct, 3-D image of the preoperative candidate's body may be used.

As further shown in FIG. 2, a specialized MEP has been applied to the scanned image 200 and certain measurement lines 210 have been applied to the preoperative scanned image 200 at, for example, the patient's chest, bust, underbust, waist, hips, abdomen, and stomach.

The chart 300, as shown in FIG. 3, shows an exemplary summary of certain of the measurement results from the MEP file.

Figure 4:
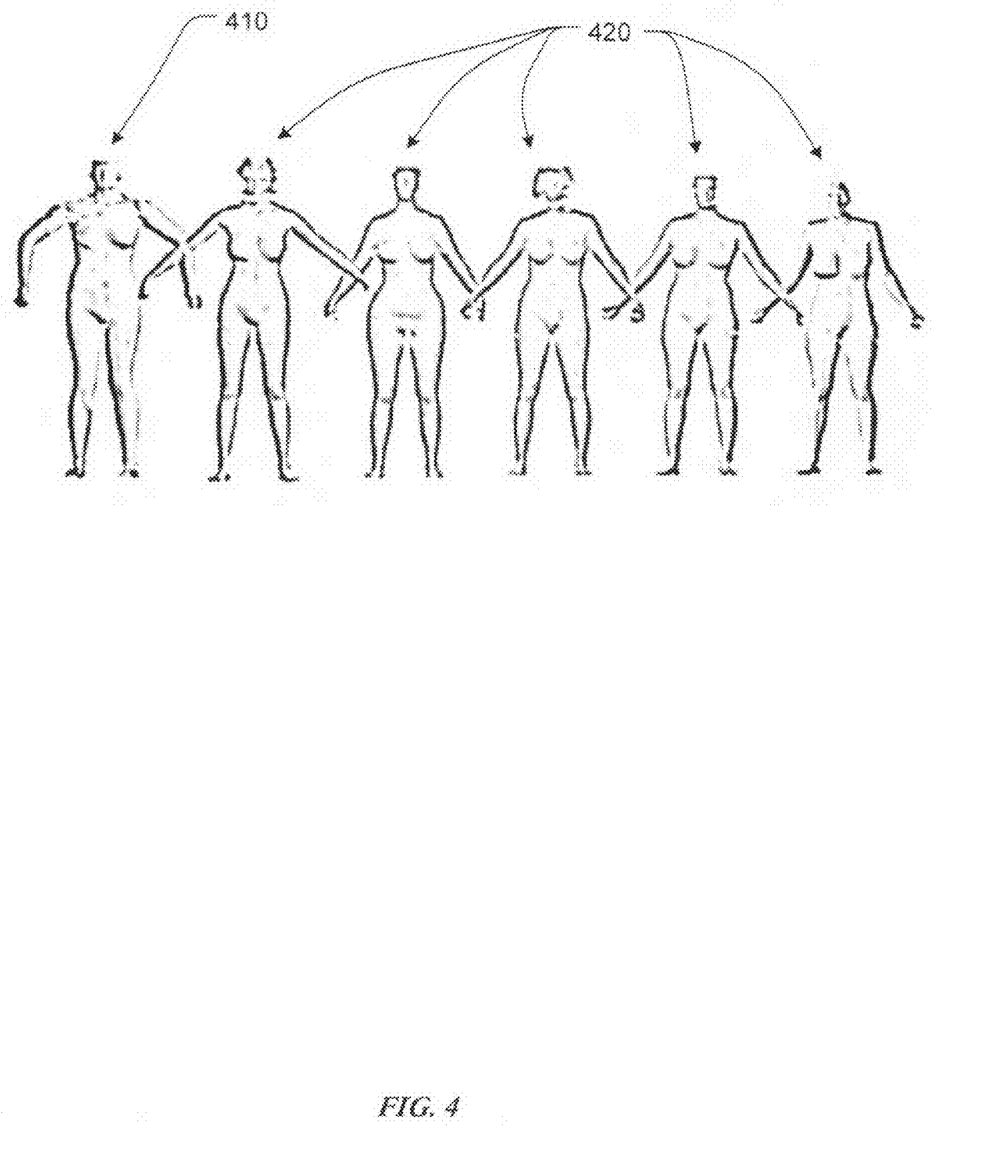
FIG. 4 shows an exemplary embodiment of the postoperative breast augmentation patients chosen for virtual surgery on the preoperative image, according to this invention.

FIG. 4 shows an exemplary embodiment of the postoperative breast augmentation patient images 420 chosen for comparison to the preoperative image 410, according to this invention.

As shown in FIG. 4, the preoperative candidate's image 410 and the postoperative breast augmentation patient images 420 are profiled and displayed. It should be appreciated that, as shown in FIG. 4, the preoperative candidate's image 410 and the postoperative breast augmentation patient images 420 have each been converted from the scan image format to a 3-D image format.

The particular postoperative breast augmentation patient images 420 have been selected from a postoperative catalog database for comparison to the preoperative candidates image 410 based on previously scanned and measured postoperative breast augmentation patients whose key measurements, as determined by an MEP file, are similar to the key measurements and additional information of the preoperative candidate, as discussed above, with respect to FIGS. 1A and 1B.

Figure 5:
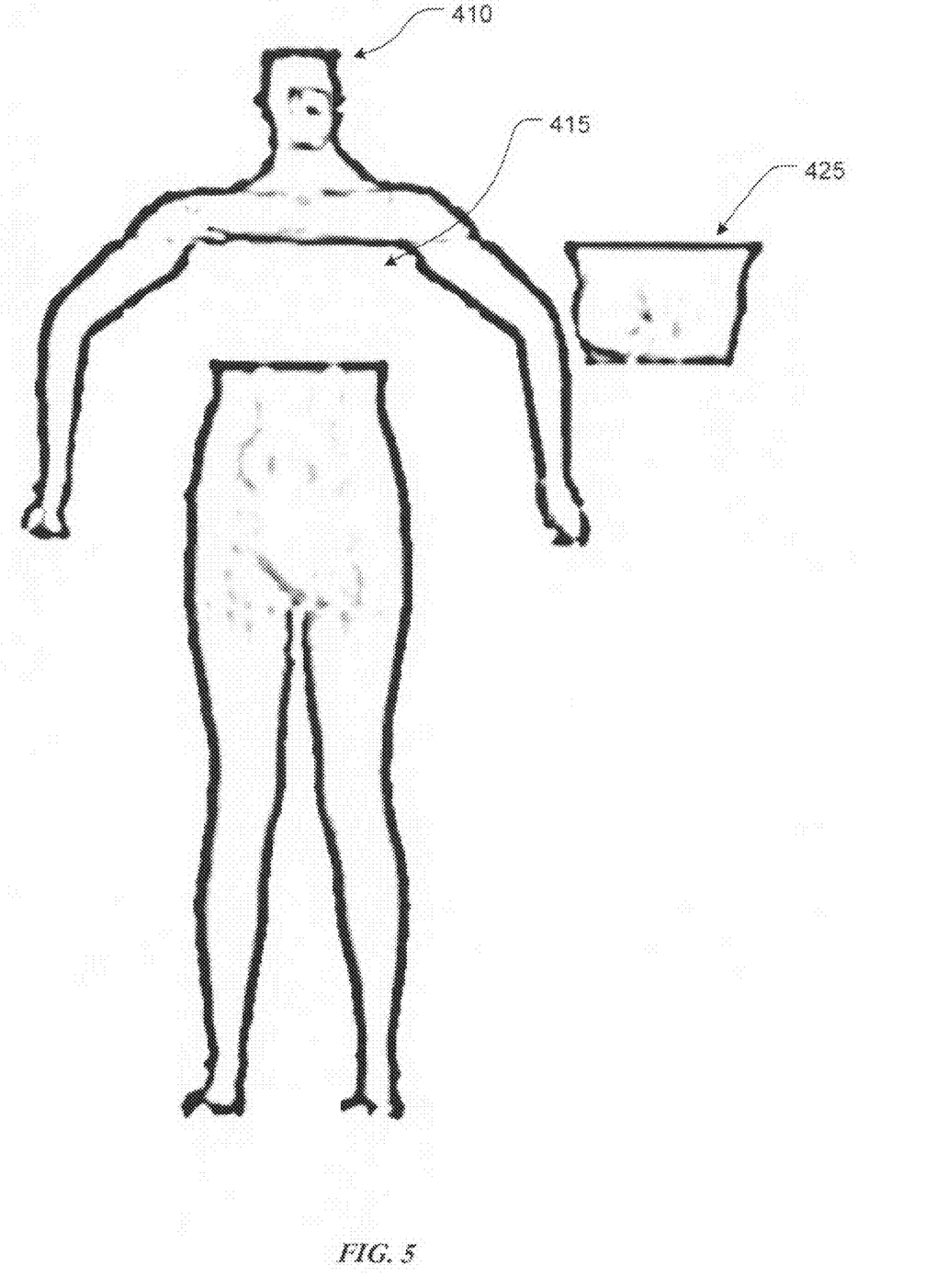
FIG. 5 shows an exemplary embodiment of a retained breast section of the postoperative breast augmentation patient and a deleted breast section of the preoperative candidate image according to this invention.

FIG. 5 shows an exemplary embodiment of a retained breast section 425 of a postoperative breast augmentation patient and a deleted breast section 415 of the preoperative candidate image 410 according to this invention.

As shown in FIG. 5, the preoperative candidate's scanned image and a selected postoperative breast augmentation patients' scanned image have been converted from a scanned image format to a 3-D image format and imported into a 3-D image editor.

Using the 3-D image editor, an appropriate breast section 415 has been extracted from the torso of the preoperative candidate's 3-D image 410 and an appropriate breast section 425 has been extracted from the torso of a selected postoperative breast augmentation patient's 3-D image, as discussed above, with respect to FIGS. 1A and 1B.

In various exemplary embodiments, the extracted sections are measured prior to dissection, ensuring minimal overlap when the breast section 425 of the postoperative patient is grafted in place of the deleted breast section 415 of the preoperative candidate's 3-D image 410.

Figure 6:
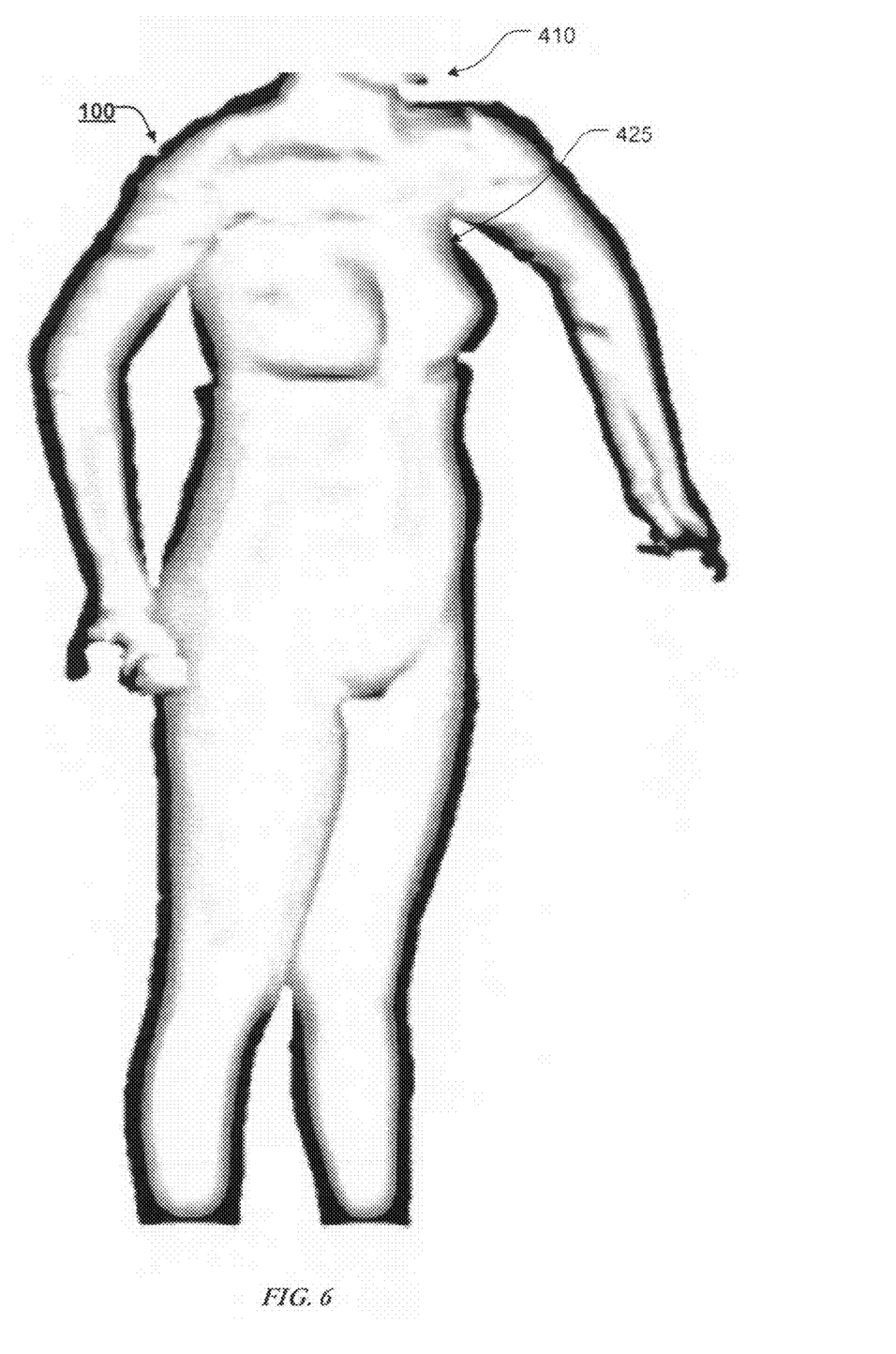
FIG. 6 shows an exemplary embodiment of the postoperative breast augmentation patient's breast section aligned within the preoperative candidate's 3-D image according to this invention.

FIG. 6 shows an exemplary embodiment of the postoperative breast augmentation patient's breast section 425 aligned within the preoperative candidate's 3-D image 410 according to this invention.

As illustrated in FIG. 6, the postoperative breast augmentation patient's breast section 425 comprises symmetric, 410 cc implants in the right and left breast area. The breast section 425 has been aligned within the preoperative candidate's 3-D image 410, as discussed above, with respect to FIGS. 1A and 1B.

As further illustrated in FIG. 6, the alignment clearly shows the dimensional differences between the postoperative breast augmentation patient's breast section 425 and the preoperative candidate's torso.

Figure 7:
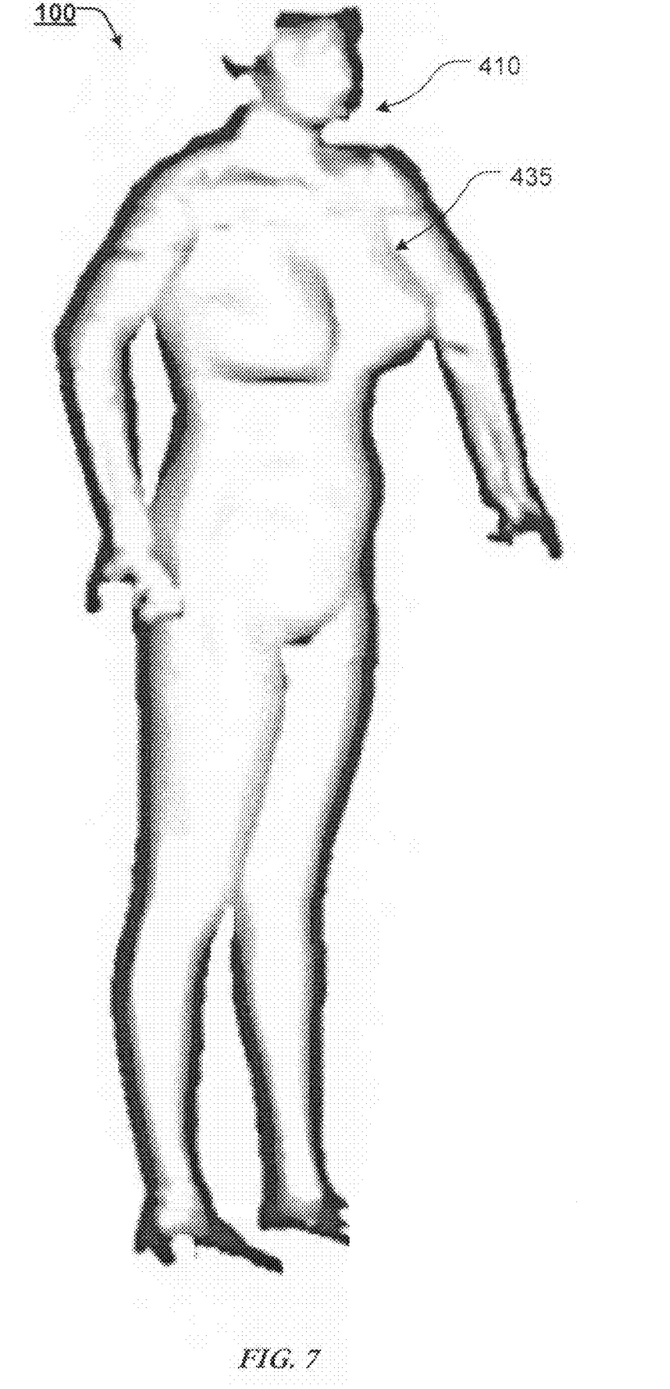
FIG. 7 shows an exemplary embodiment of a postoperative breast augmentation patient's breast section scaled to match the torso dimensions of the preoperative candidate's torso according to this invention.

FIG. 7 shows an exemplary embodiment of a postoperative breast augmentation patient's breast section 425 scaled to match the torso dimensions of the preoperative candidate's torso according to this invention.

As illustrated in FIG. 7, because of the dimensional differences between the postoperative breast augmentation patient's breast section 425 and the preoperative candidate's torso, as shown in FIG. 6, the postoperative breast augmentation patient's breast section 425 has been scaled, as discussed above, with respect to FIGS. 1A and 1B, to match the dimensions of the torso of the preoperative candidate's 3-D image 410 and to create a scaled breast section 435.

Since, in this embodiment, proportional scaling is used, the implant sizes of the postoperative breast augmentation patient's implants are also proportionally scaled. Thus, the 410 cc implants shown in the right and left breast area of the postoperative breast augmentation patient's breast section 425, of FIG. 6, have been scaled proportionally, by a factor of 1.3, such that the scaled breast section 435 shows the preoperative candidate's 3-D image 410 with 530 cc, symmetric implants.

Figure 8:
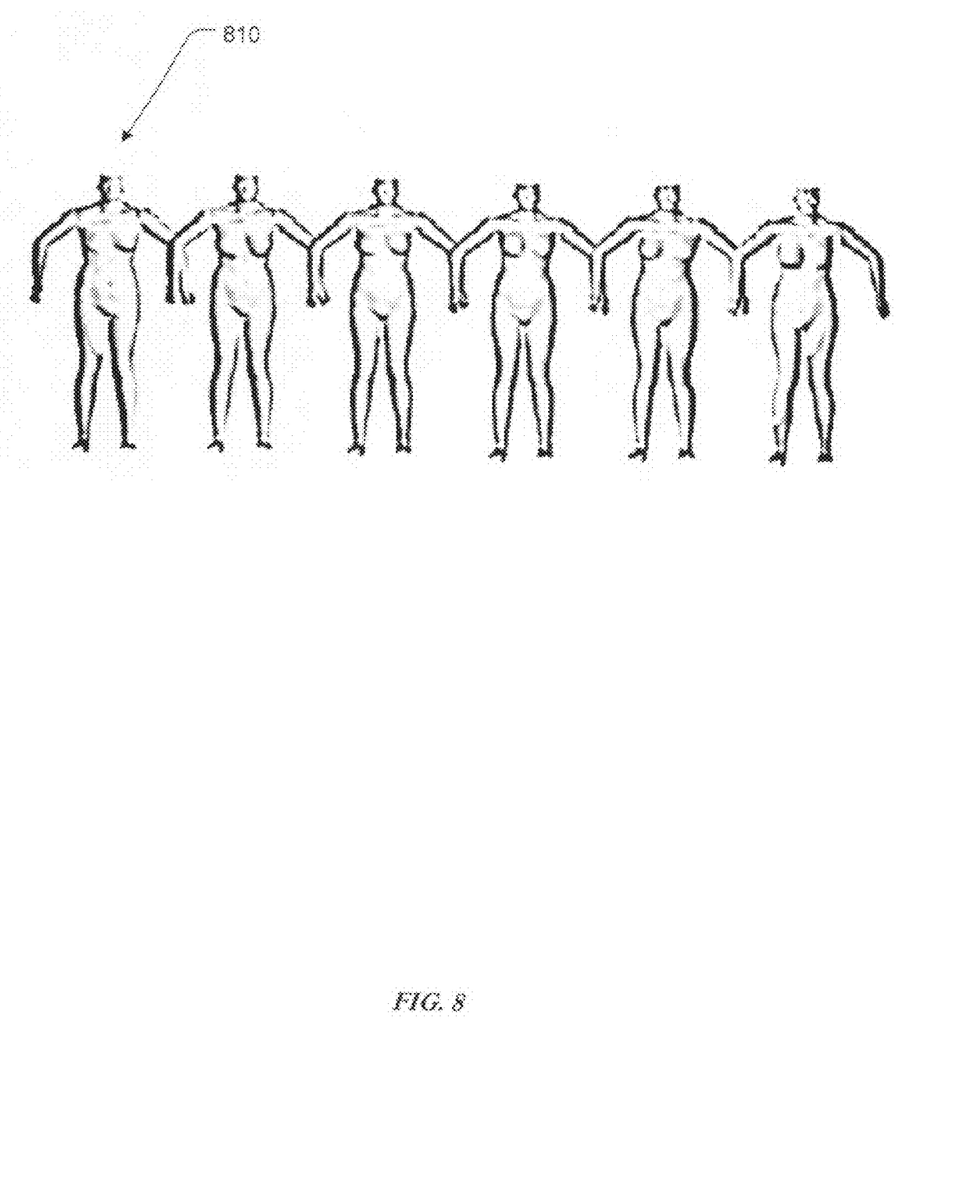
FIG. 8 shows an exemplary embodiment of a composite view of forecasted 3-D images based on postoperative breast augmentation patients, according to this invention.

FIG. 8 shows an exemplary embodiment of a composite view of forecasted 3-D images based on postoperative breast augmentation patients, according to this invention.

As illustrated in FIG. 8, the method described above, with respect to FIGS. 5-7 is duplicated for the remaining one or more appropriate postoperative breast augmentation patients that were selected from the postoperative catalog database to produce a corresponding forecasted 3-D image for each selected postoperative breast augmentation patient. Each forecasted 3-D image will reflect at least slightly different breast augmentation sizes based on selections from the postoperative breast augmentation catalog. Thus, because of the different implant sizes, each forecasted 3-D image will produce a different aesthetic look.

The forecasted 3-D images may then be viewed by the patient and/or the surgeon, such that a specific forecasted 3-D image, which most closely meets the desires of the patient and the surgical guidelines, may be selected for further comparison and review.

Figure 9:
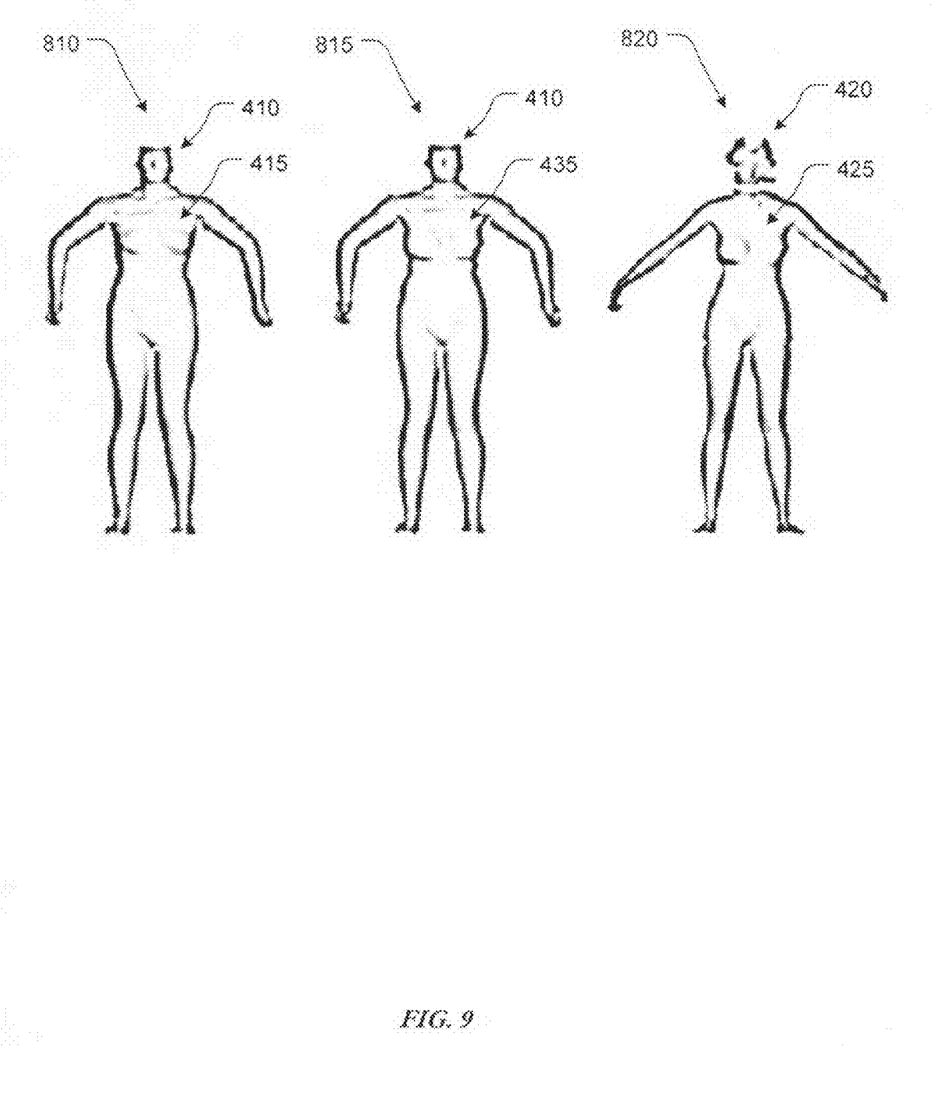
FIG. 9 shows an exemplary comparison of the preoperative candidate's 3-D image, the preoperative candidate's selected forecasted 3-D image, and the selected postoperative patient image 820.

FIG. 9 shows an exemplary comparison of the preoperative candidate's 3-D image 410 with the preoperative breast section 415 (preoperative candidate image 810), the preoperative candidate's selected 3-D image 410 with the scaled breast section 435 (selected forecasted image 815), and the selected postoperative breast augmentation patient image 420 with the un-scaled postoperative breast augmentation patient's breast section 425 (postoperative patient image 820).

As illustrated in FIG. 9, the postoperative patient image 820 shows the results of implantation of 410 cc implants in the right and left breast of the postoperative breast augmentation patient's breast section 425. To create the selected forecasted image 815, the 410 cc implants of the breast section 425 were aligned within the preoperative candidate's 3-D image 410 and scaled, according to this invention, resulting in the selected forecasted image 815 forecasting the results of implantation of 530 cc, symmetric implants, in the right and left breast of the preoperative candidate's 3-D image 410.

Once the selected forecasted image 815 is created, the forecasted image is converted to a scanner readable and measurable format.

Figure 10:
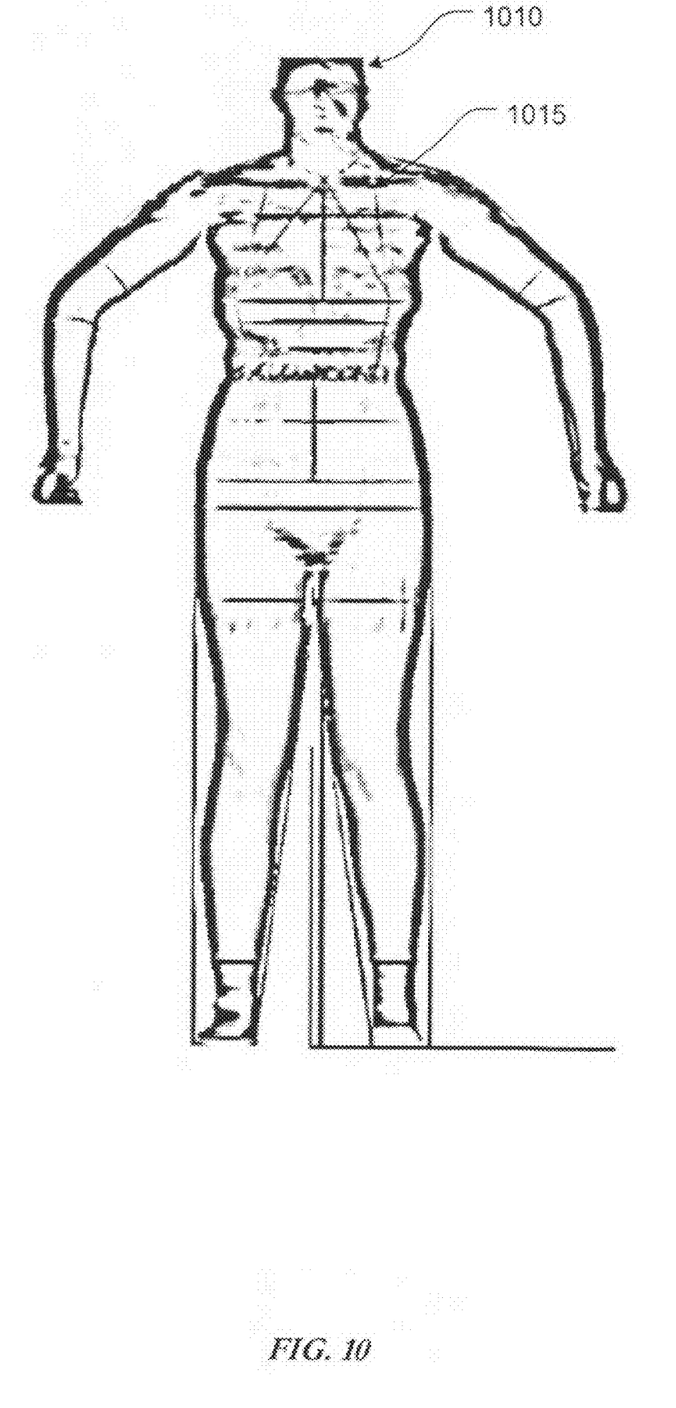
FIG. 10 shows an exemplary embodiment of the selected forecasted image converted to a scanner readable and measurable format to produce a converted forecasted 3-D image, according to this invention.
Figure 11:
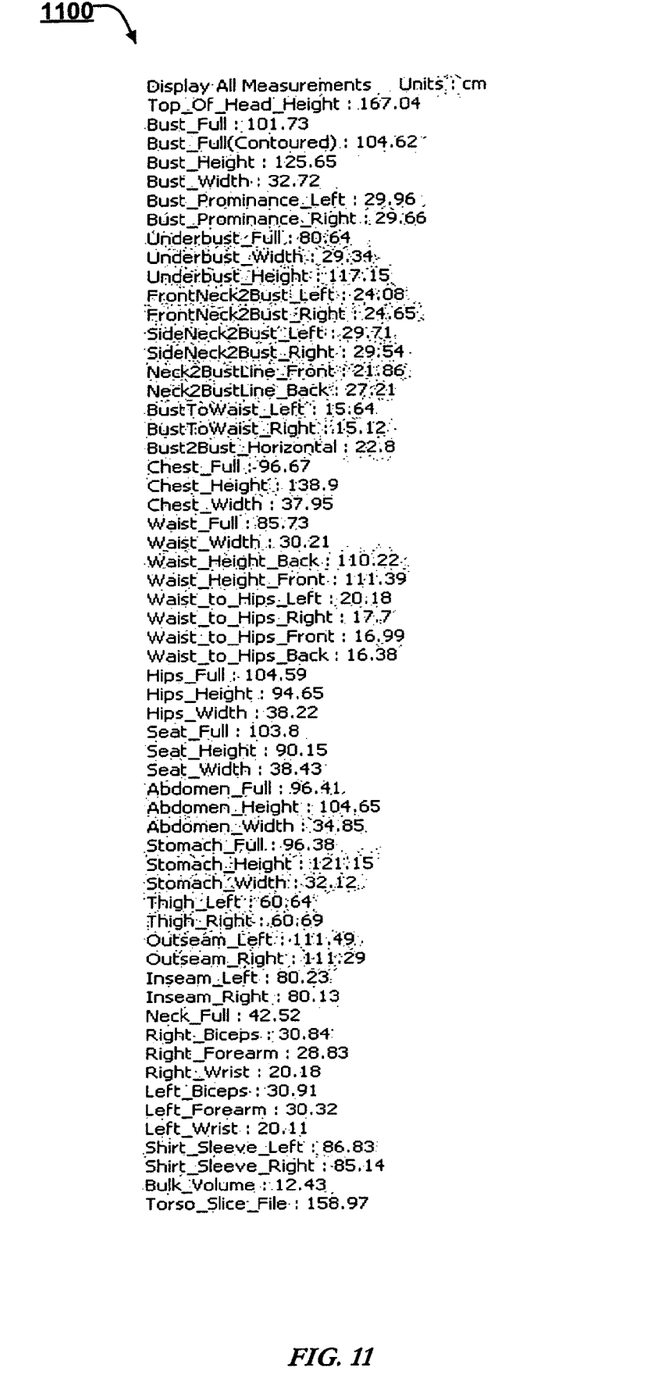
FIG. 11 shows a chart outlining forecasted measurements extrapolated from the converted forecasted 3-D image of FIG. 10, according to this invention.

FIG. 10 shows an exemplary embodiment of the selected forecasted image 815 converted to a scanner readable and measurable format, as discussed above, to produce a converted forecasted 3-D image 1010, according to this invention. FIG. 11 shows a chart 1100 outlining forecasted measurements extrapolated from the converted forecasted 3-D image 1010 of FIG. 10, according to this invention.

As further shown in FIG. 10, the MEP has been applied to the converted forecasted 3-D image 1010 and certain measurement lines 1015 have been applied to the converted forecasted 3-D image 1010 at, for example, the patient's chest, bust, underbust, waist, hips, abdomen, and stomach.

The chart 1100, as shown in FIG. 11, shows an exemplary summary of certain of the measurement results from the MEP file.

Once the specific measurements of the converted forecasted 3-D image 1010 have been calculated, the converted forecasted 3-D image 1010 and the measurements become part of the preoperative candidate's digital archive. If the preoperative candidate does have the surgical procedure, postoperative scans of the preoperative candidate may be compared to the converted forecasted 3-D image 1010 and the measurements for validation and so that any discrepancies may be identified.

Figure 12:
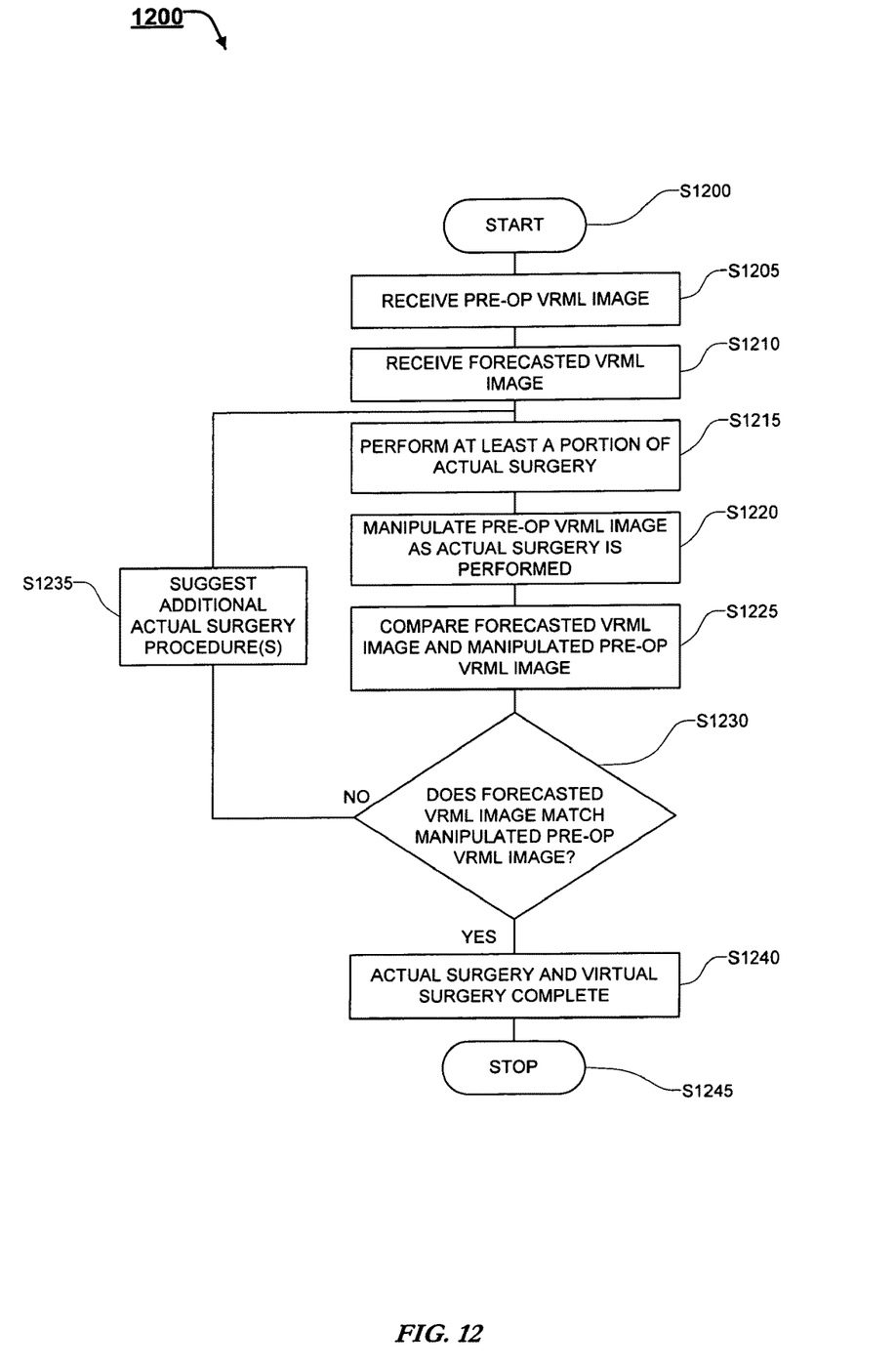
FIG. 12 shows a flowchart outlining one illustrative, non-limiting embodiment of a method for performing a virtual surgery to assist an actual surgery according to this invention.

FIG. 12 shows a flowchart 1200 outlining one illustrative, non-limiting embodiment of a method for performing a virtual surgery to assist an actual surgery according to this invention.

As shown in FIG. 12, the exemplary method begins in step S1200 and continues to Step S1205 wherein the preoperative candidate's 3-D image is received. It should be appreciated that certain measurements and other medical information may be received in addition to the preoperative candidate's 3-D image.

Then, in Step S1210, a selected forecasted 3-D image is received. It should be appreciated that certain measurements and other medical information may be received in addition to the selected forecasted 3-D image.

Next, in Step S1215, at least a portion of the actual surgery is performed on the preoperative candidate. It should be appreciated that the surgery performed is a cosmetic and/or reconstructive surgical procedure, the outcome of which is forecasted by the forecasted 3-D image.

In Step S1220, the preoperative candidate's 3-D image is manipulated, as the portion of the actual surgery is performed, to reflect the actual changes being made to the preoperative candidate's body. For example, as a surgeon places a 410 cc implant in the candidate's left breast, the preoperative candidate's 3-D image is manipulated to include a 410 cc implant in the candidate's left breast. In this manner, the surgeon may view, via the updated 3-D image, the results of the each step in the actual surgery and may choose to augment the surgical procedure to produce a better result for the candidate.

In Step S1225, the preoperative candidate's manipulated 3-D image is compared to the received forecasted 3-D image. It should be appreciated that certain measurements and other medical information may be compared between the preoperative candidate's manipulated 3-D image and the received forecasted 3-D image.

In Step S1230, a determination is made whether at least a relevant portion of the preoperative candidate's manipulated 3-D image matches the received forecasted 3-D image. It should be appreciated that determination may be based upon certain of the measurements and other medical information that is included with the preoperative candidate's manipulated 3-D image and the received forecasted 3-D image.

It should also be appreciated that, in certain exemplary embodiments, the preoperative candidate's manipulated 3-D image will not be required to match the received forecasted 3-D image exactly in order for a match to be determined. Certain acceptable parameters may be established such that an exact match is not required.

If, in Step S1230, it is determined that the at least relevant portion of the preoperative candidate's manipulated 3-D image does not match the received forecasted 3-D image, the method advances to Step S1235.

In Step S1235, certain suggestions may be provided to propose possible procedures to be performed such that the candidate's body will more closely match the forecasted 3-D image. These suggestions may be provided as a 3-D or other image or may be provided as measurement, weight, or volume information.

When the suggestions have been provided, the method returns to Step S1215, and a further portion of the actual surgery is performed on the preoperative candidate.

It should also be appreciated that in various exemplary embodiments, Step S1235 is not included. In these exemplary embodiments, if it is determined in Step S1230 that the at least relevant portion of the preoperative candidate's manipulated 3-D image does not match the received forecasted 3-D image, the method returns to Step S1215, and a further portion of the actual surgery is performed on the preoperative candidate, without any provided suggestions.

If, in Step S1230, it is determined that the at least relevant portion of the preoperative candidate's manipulated 3-D image does match the received forecasted 3-D image, the method advances to Step S1240.

In Step S1240, both the actual surgery and the companion virtual surgery are complete.

The method then advances to S1245 and the method ends.

It should be appreciated that the preoperative candidate's digital archive, if established, may be updated to include information and/or images for each iteration of the actual and virtual surgery procedure.

While this invention has been described in conjunction with the exemplary embodiments outlined above, it is evident that many alternatives, modifications, and variations will be apparent to those skilled in the art. For example, the embodiments of this invention have been described with reference to the prediction, evaluation, and validation of an exemplary breast augmentation surgical procedure. However, it should be appreciated that the virtual surgery systems, methods, and apparatuses of this invention may be utilized in various other cosmetic and reconstructive surgical procedures. Such adaptations and modifications should and are intended to be comprehended within the meaning and range of equivalents of the disclosed exemplary embodiments.

It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A method for performing a virtual surgery to assist an actual surgery, comprising:

receiving a preoperative candidate's 3-D image;

receiving a selected forecasted 3-D image;

allowing at least a portion of the actual surgery to be performed on the preoperative candidate's body, wherein a proposed outcome of the actual surgery is forecasted by the forecasted 3-D image;

manipulating the preoperative candidate's 3-D image to reflect the actual changes made to the preoperative candidate's body as a result of the performed portion of the actual surgery;

comparing the preoperative candidate's manipulated 3-D image to the received forecasted 3-D image;

determining whether at least a portion of the preoperative candidate's manipulated 3-D image matches the received forecasted 3-D image;

allowing, if it is determined that the preoperative candidate's manipulated 3-D image does not match the received forecasted 3-D image, a further portion of the actual surgery to be performed on the preoperative candidate's body; and completing, if it is determined that the preoperative candidate's manipulated 3-D image does match the received forecasted 3-D image, the actual surgery.

2. The method of claim 1, wherein receiving a preoperative candidate's 3-D image includes receiving measurement and other medical information in addition to the preoperative candidate's 3-D image.

3. The method of claim 1, wherein receiving a selected forecasted 3-D image includes receiving measurement and other medical information in addition to the forecasted 3-D image.

4. The method of claim 1, wherein comparing the preoperative candidate's manipulated 3-D image to the received forecasted 3-D image includes comparing certain measurements and other information between the preoperative candidate's manipulated 3-D image and the received forecasted 3-D image.

5. The method of claim 1, wherein determining whether at least a portion of the preoperative candidate's manipulated 3-D image matches the received forecasted 3-D image includes determining based upon certain measurements and other information included with the preoperative candidate's manipulated 3-D image and the received forecasted 3-D image.

6. The method of claim 1, wherein determining whether at least a portion of the preoperative candidate's manipulated 3-D image matches the received forecasted 3-D image includes determining whether at least a portion of the preoperative candidate's manipulated 3-D image matches the received forecasted 3-D image, within a predetermined parameter, such that an exact match is not required.

7. The method of claim 1, further including receiving information regarding at least one proposed procedure to be performed as part of the actual surgery such that the preoperative candidate's body will more closely match the forecasted 3-D image.

8. The method of claim 7, wherein the information is provided as image, measurement, weight, or volume information.

9. The method of claim 1, further including storing information and/or images for each iteration of the actual or virtual surgery procedure in a digital archive.

\* \* \* \* \*